(12) United States Patent
Dennis

(10) Patent No.: US 7,121,279 B2
(45) Date of Patent: Oct. 17, 2006

(54) RESPIRATORY MASK

(76) Inventor: Carnell K. Dennis, 2406 Jacqueline Dr., Apt. B48, Wilmington, DE (US) 19810

( * ) Notice: Subject to any disclaimer, the term of this patent is extended or adjusted under 35 U.S.C. 154(b) by 93 days.

(21) Appl. No.: 10/766,413

(22) Filed: Jan. 28, 2004

(65) Prior Publication Data

US 2004/0182396 A1    Sep. 23, 2004

Related U.S. Application Data

(63) Continuation-in-part of application No. 10/041,523, filed on Jan. 8, 2002, now Pat. No. 6,851,428.

(51) Int. Cl.
*A62B 18/08* (2006.01)
*A62B 18/02* (2006.01)
*A62B 9/00* (2006.01)
*A62M 16/06* (2006.01)

(52) U.S. Cl. .................. 128/206.21; 128/203.29; 128/205.25

(58) Field of Classification Search ........... 128/201.24, 128/205.25–207.18
See application file for complete search history.

(56) References Cited

U.S. PATENT DOCUMENTS

| 2,382,364 | A | * | 8/1945 | Yant ...................... 128/201.19 |
| 3,441,020 | A | * | 4/1969 | Wortz et al. ........... 128/205.25 |
| 3,977,432 | A | | 8/1976 | Vidal |
| 4,657,010 | A | * | 4/1987 | Wright .................. 128/205.25 |
| 4,739,755 | A | * | 4/1988 | White et al. ........... 128/206.12 |
| 4,793,342 | A | | 12/1988 | Haber et al. |
| 5,050,594 | A | | 9/1991 | Babb |
| 5,353,789 | A | * | 10/1994 | Schlobohm ............ 128/206.24 |
| 5,673,690 | A | | 10/1997 | Tayebi et al. |
| 5,921,239 | A | | 7/1999 | McCall et al. |
| 6,474,336 | B1 | | 11/2002 | Wolfe |
| 6,851,428 | B1 | * | 2/2005 | Dennis .................. 128/205.25 |

* cited by examiner

*Primary Examiner*—Glenn K. Dawson
(74) *Attorney, Agent, or Firm*—Connolly Bove Lodge & Hutz LLP

(57) ABSTRACT

A respiratory mask is reduced in size to better fit patients with smaller faces by folding accordion folds of the mask. An adjustment member allows for selective folding of the accordion folds, thereby determining the size of the mask. The respiratory mask can thus be adjusted to fit both larger and smaller persons.

19 Claims, 4 Drawing Sheets

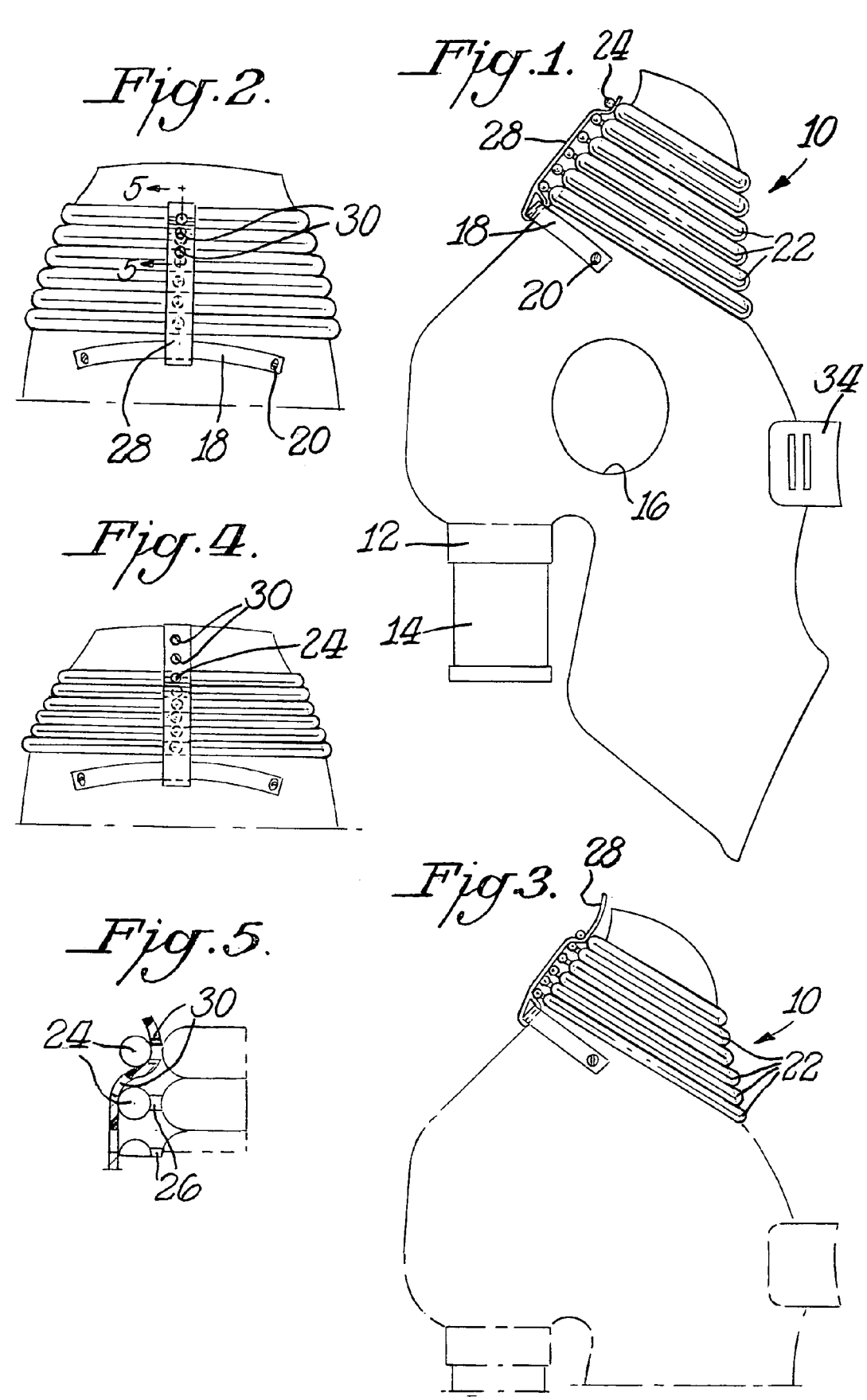

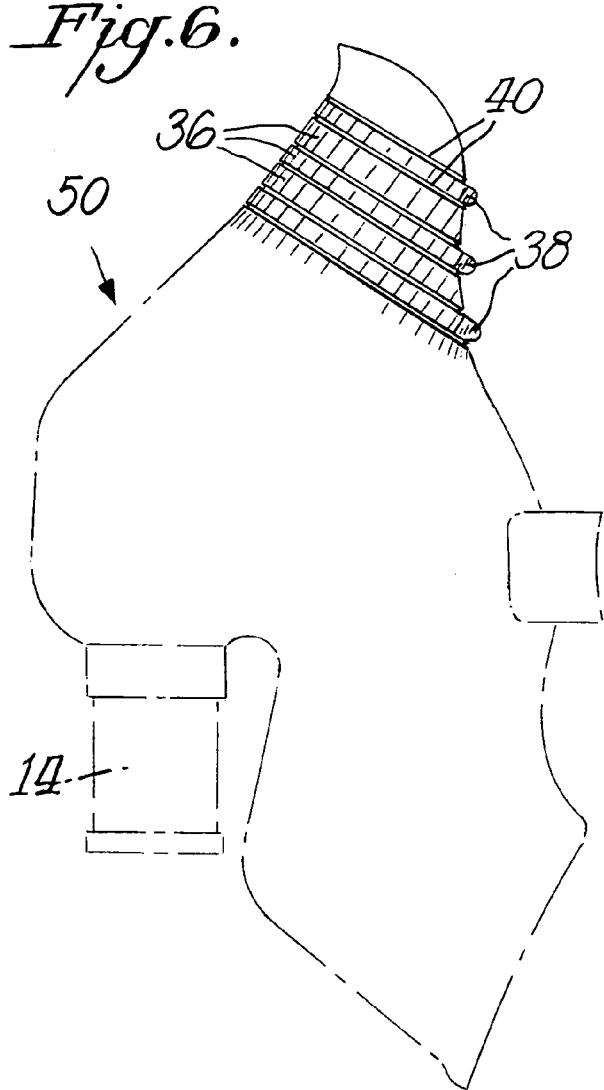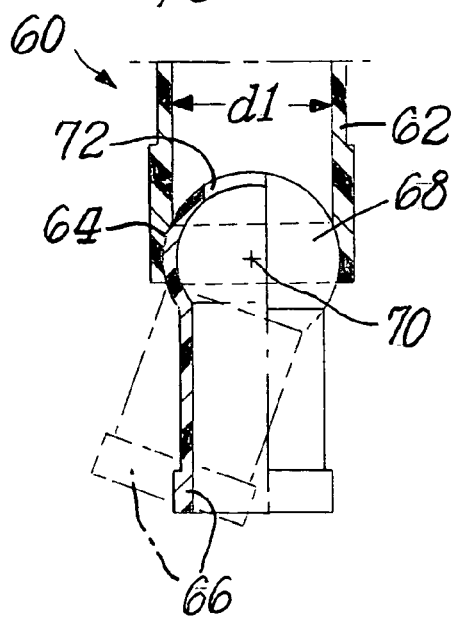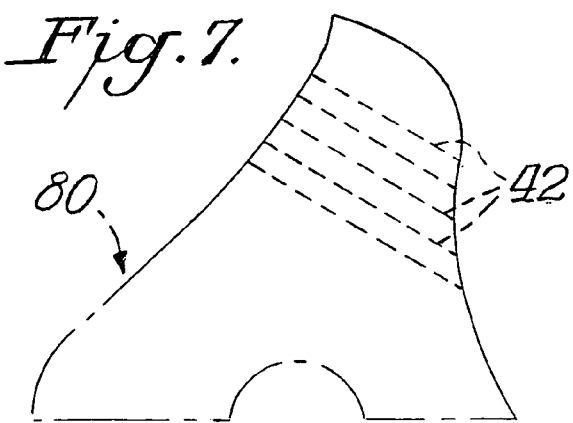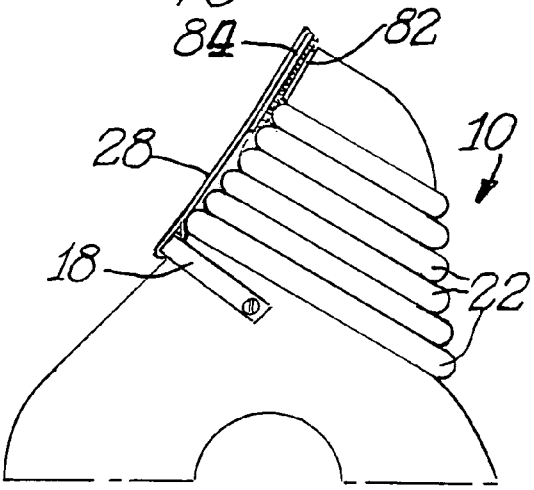

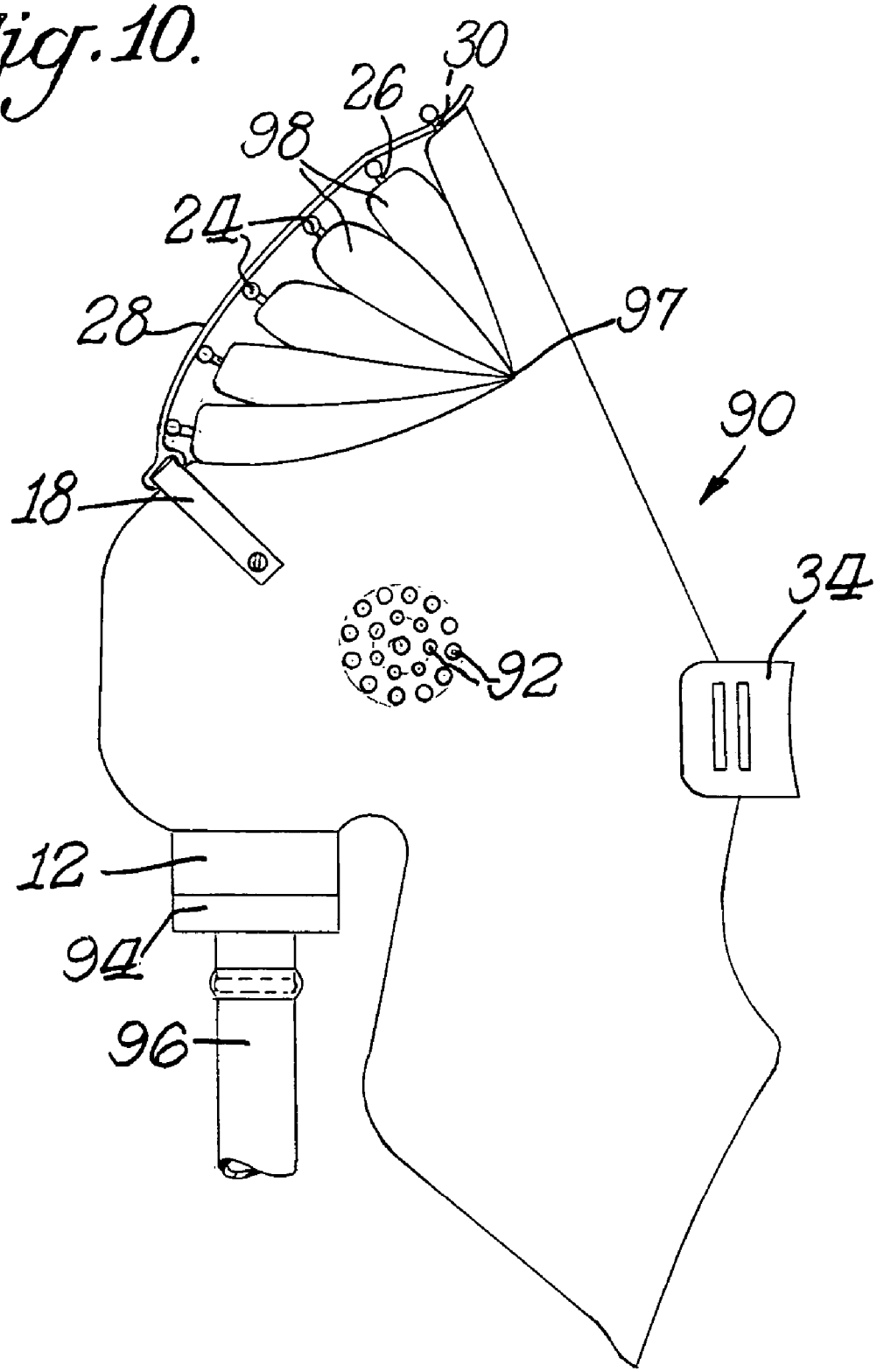

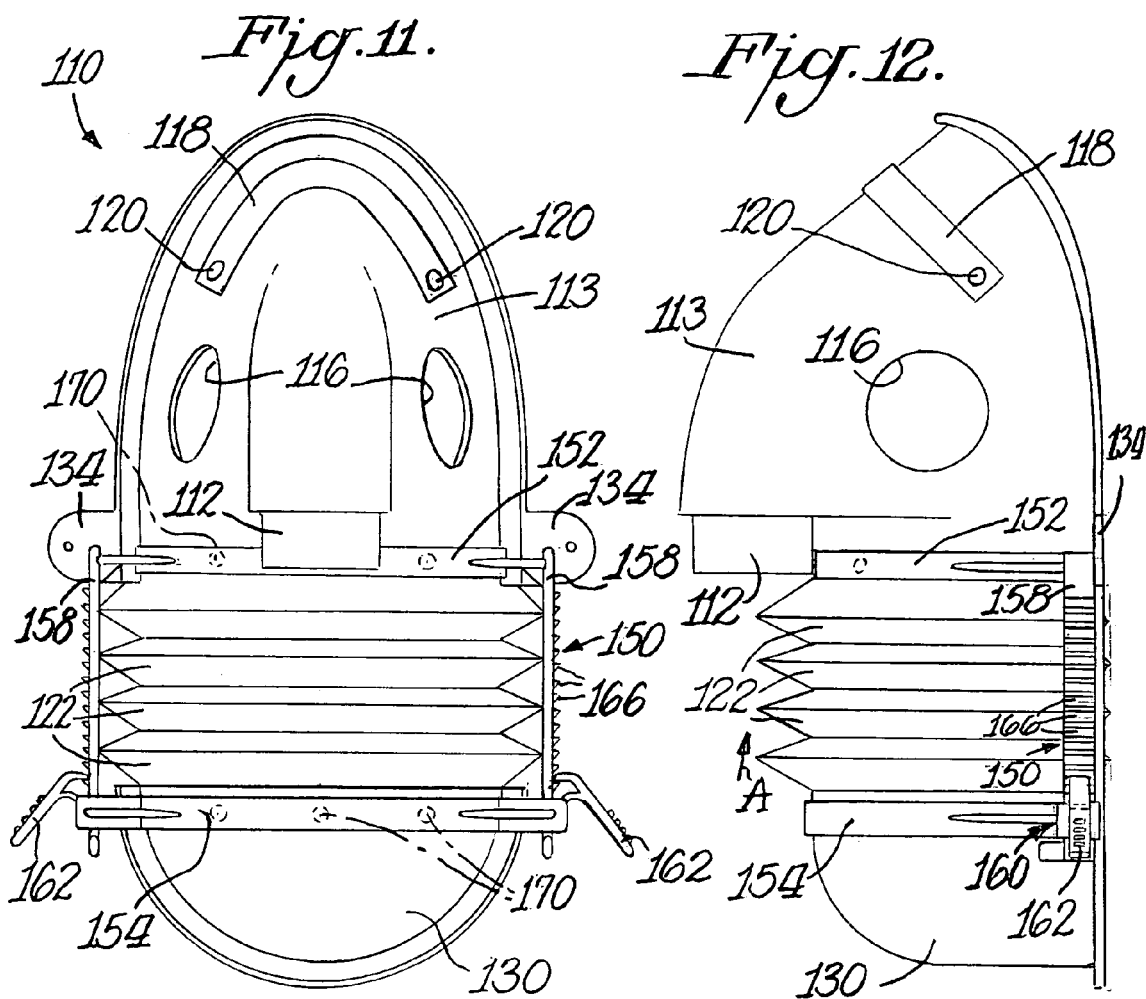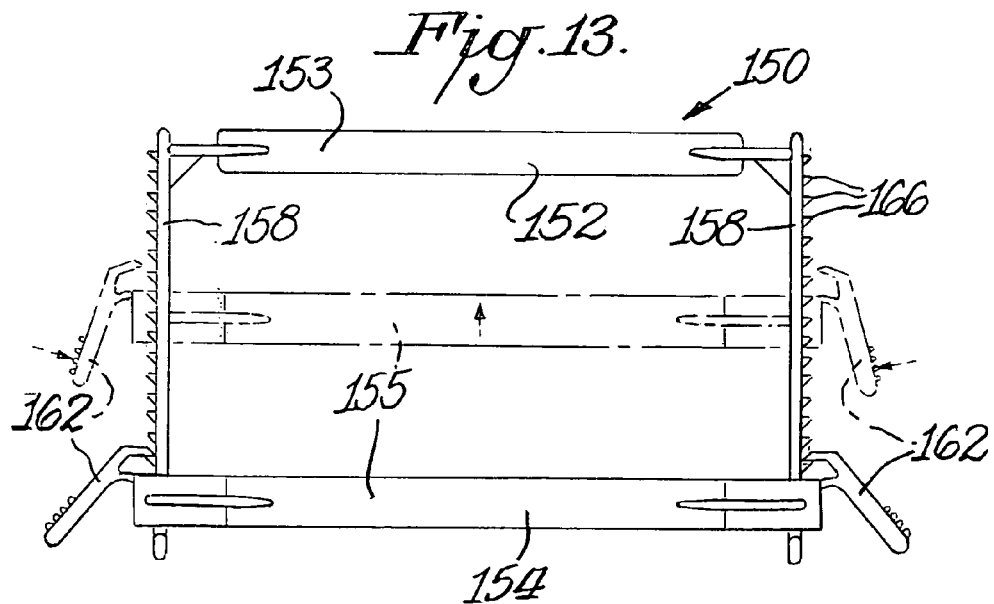

RESPIRATORY MASK

RELATED APPLICATION

This application is a continuation-in-part of application Ser. No. 10/041,523, entitled "SIZE-ADJUSTABLE RESPIRATORY MASK" and filed Jan. 8, 2002, now U.S. Pat. No. 6,851,428 the entire contents of which are hereby incorporated by reference.

FIELD OF THE INVENTION

The present invention relates to respiratory masks used to administer treating gases or medications to patients. A representative treating gas is oxygen, and a representative medication is an aerosol for asthma treatment.

BACKGROUND OF THE INVENTION

Hospitals and respiratory therapists administer treating gases to individual patients by placing a respiratory mask over the patient's nose and mouth. The masks are supplied in standard sizes intended for adults and children. However, many adult patients have smaller facial dimensions such that the standard sizes do not fit properly, at best making the mask uncomfortable and at worst leading to ineffective administration of treating gases. In addition, many children have smaller facial dimensions such that the standard mask sizes provided for children do not fit them. Hence, an adjustable-size respiratory mask is needed to fit patients with smaller facial dimensions.

U.S. Pat. No. 4,657,010 discloses an adjustable face mask in which the bottom of the mask may be extended lengthwise by fastening a separate extension portion (lower portion 14) to the mask. The lower portion 14 is provided with snap closures 42 that mate with eyelet holes 40 in the upper portion of the mask. The separate extension portion is awkward, and size adjustments can not effectively be made while the mask is in place over a patient's face. Most patient discomfort is caused when a too large size mask covers their eyes and/or forehead, making the bottom portion size adjustment in this prior patent less helpful when trying to solve the problems associated with over-sized respiratory masks. Moreover, the separate extension portion is more apt to be disconnected or lost before or during use.

SUMMARY OF THE INVENTION

A size-adjustable respiratory mask has a plurality of accordion folds formed between upper portion and a lower portion of the mask. The accordion folds have an open position which is most suited when the mask is to be used for an average or larger size adult, and a folded position most suited for when the mask is to be used for a smaller person. An adjustment member is used to adjust the length of the mask by folding the accordion folds.

The accordion fold may be formed by one or more ribs connected by a flexible material, or by one or more tubes connected by a flexible material. In the most preferred embodiment, the accordion fold is formed integrally with the lower portion of the mask. The entire mask can be formed of a single piece of plastic material of constant thickness.

The mask may be constructed from one or more resilient plastic materials that are known as suitable for medical applications. Preferably, the mask material is latex free and free of other known allergens. Preferably, the mask is constructed from one or more of the following materials: thermoplastic resins, polyurethane resins, poly(vinyl chloride), polypropylene, polyethylene, polystyrene, SURLYN® from E.I. DuPont de Nemours & Company, Inc., or other plastics. A particularly preferred poly(vinyl chloride) is VM 1775 NT Clear 0001 from Maclin Company of City of Industry, Calif.

DESCRIPTION OF THE FIGURES

FIG. 1 is a side elevational view of a respiratory mask according to a first embodiment of the invention as sized for an average adult patient;

FIG. 2 is a fragmental front elevational view of the respiratory mask of FIG. 1;

FIG. 3 is a side elevational view of a respiratory mask according to the invention as adjusted in size for a smaller adult patient;

FIG. 4 is a fragmental front elevational view of the respiratory mask of FIG. 3;

FIG. 5 is a cross-sectional view taken along line 5—5 of FIG. 2 showing size-adjusting means as a button held within an opening in a strap;

FIG. 6 is a side elevational view of a respiratory mask according to a second alternate embodiment of the invention;

FIG. 7 is a fragmental side elevational view of the respiratory mask of FIG. 6;

FIG. 8 is a fragmental partial cross-sectional view showing a ball swivel joint connector engaged within the tubular inlet of a respiratory mask;

FIG. 9 is a fragmental side elevational view of a respiratory mask according to a third alternate embodiment of the invention;

FIG. 10 is a side elevational view of a respiratory mask according to a fourth alternate embodiment of the invention;

FIG. 11 is a front elevational view of a respiratory mask according to a fifth alternate embodiment;

FIG. 12 is a side elevational view of the respiratory mask of FIG. 11; and

FIG. 13 is an isolated view of an adjustment member of the respiratory mask of FIG. 11.

DESCRIPTION OF THE PREFERRED EMBODIMENTS

Referring first to FIG. 1, a respiratory mask 10 includes a mask portion for covering the nose and mouth of a patient receiving a respiratory treatment, such as oxygen or a medicative aerosol or vapor. The mask 10 includes a tubular inlet 12 proximate the nose portion of the mask. A connector 14 is attached to the tubular inlet 12. A nebulizer (not shown) for delivering the respiratory treatment is in turn attached to the connector 14. The mask 10 further defines one or more exhaust ports 16, which are preferred when a mask is used for aerosol or vapor treatments. Head strap brackets 34 are attached to the lateral edges of the mask 10. One or more elastic head straps (not shown) are threaded through the brackets and wrap around the patient's head to hold the mask in place during treatment.

The mask 10 is provided with means for adjusting mask size. As shown in FIG. 1, the mask 10 is configured for a normal size adult male. The mask 10 is provided with a deformable metal strap 18 attached by snaps 20. The metal strap 18 can be bent over the bridge of the patient's nose to help hold the mask in place during treatment.

Accordion folds 22 are provided in a parallel array at the top of the nose portion of the mask 10. Each accordion fold comprises a rib or tube of stiffer material than the more resilient plastic material used to form the body of the mask. Each rib or tube is connected by lateral edge to an adjacent rib or tube. When expanded, as shown in FIG. 1, the mask 10 is of a size suitable for an adult male. Preferably, as shown in FIG. 1, the accordion folds 22 are integral with the material forming the top portion of the mask 10.

A snap or button 24 is associated with each accordion fold 22. The buttons 24 are mounted on pins 26 to separate slightly the buttons from the edges of the accordion folds 22. A band 28 is connected to the deformable metal strap 18 at its proximal end and defines one or more openings 30 at its distal end. The band 28 is formed from poly(vinyl chloride) resin or plastic material. Preferably, the band 28 has a thickness comparable to the distance of separation between the buttons 24 and the accordion folds 22. As shown in FIGS. 1, 2 and 5, the uppermost button is held within the most distant hole in the band 28. It would also be possible to leave the distal portion of the band 28 unattached to any button 24 associated with the accordion folds. In the preferred embodiment, the accordion folds 22 can be expanded to a fully open position such that the mask is suitable for use by a larger adult.

The means for attaching the band 28 to a button 24 associated with an accordion fold 22 is shown in FIG. 5. The openings 30, such as eyelet holes, have an inner diameter slightly smaller than the outer diameter of the buttons 24. Each opening or hole 30 in the band 28 can be snap fit over a button 24. The snap connection is not permanent, and an adjustment can be made readily by disconnecting the band from a particular button and reattaching to another button.

Various size adjustments are possible. Referring next to FIGS. 3 and 4, the mask 10 is shown with the accordion folds 22 folded to a closed position to reduce the mask size. In this embodiment, the third opening or hold in the band 28 engages the uppermost button, thus pulling the button and the associated accordion fold 22 tighter toward the deformable strap 18 bridging the nose portion of the mask 10. With the accordion folds 22 compressed and folded to a closed position, the mask 10 is better suited for use by a smaller adult, such as a woman weighing under 100 pounds, or by a teenager or child.

Preferably, the mask 10 is fabricated from nonallergenic materials known to be suitable for contacting a patient's skin. Such materials include: thermoplastic resins, polyurethane resins, poly(vinyl chloride), polypropylene, polyethylene, polystyrene, SURLYN® from E.I. DuPont de Nemours & Company, Inc., or other plastics. The preferred mask 10 is formed from a clear poly(vinyl chloride) resin or plastic (with a thickness of about 0.020 inch) so that a respiratory technician or health care worker can observe the patient's face while treatments are administered. A particularly preferred poly(vinyl chloride) is VM 1775 NT Clear 0001 from Maclin Company of City of Industry, Calif.

A second preferred embodiment of the respiratory mask 10 is shown in FIG. 9, wherein the band 28 is provided with a hook strip 84 of a hook and loop fastener (such as a VELCRO® fastener) and the upper surface of the mask is provided with a loop strip 82. The size of the mask 10 is then adjusted by compressing or folding the accordion folds 22 and causing the hook strip 84 to contact the loop strip 82 to fasten the band 28 to the upper surface of the mask 10 to maintain the accordion folds in a folded position.

A third preferred embodiment of the respiratory mask 50 is shown in FIGS. 6 and 7. Like parts are numbered with the same reference numerals used in FIGS. 1–5. Rather than using accordion folds 22 (e.g., FIG. 1), the mask 50 incorporates a series of tear strips 36 that have tear tabs 38 at one or both ends. Preferably, the tear strips 36 are integral with the material forming the mask 50 and are separated by grooves 40 or other discontinuities in the thickness of the material. To reduce the size of the mask 50, one of the tear strips 36 is pulled away from the mask to separate the tear strip 36 and the upper portion of the mask 50 above the strip from the remaining lower portion of the mask.

As an alternative to the grooves 40, perforations 42 (FIG. 7) may be provided in the mask material to guide the tearing away of material to reduce the size of the mask 80.

The embodiment of the invention shown in FIGS. 1–5 permits variable adjustment of the mask size from larger to smaller. Moreover, once the mask is adjusted to a smaller size, it may still be enlarged to the original adult size or any size therebetween. The embodiments of the invention shown in FIGS. 6 and 7, however, do not provide a means for returning the mask to its original adult size following the size adjustment made by removing material from the top portion of the mask. Nevertheless, the embodiments of FIGS. 6 and 7 may have fabrication or cost advantages making them suitable for many applications.

Referring next to FIG. 10, an oxygen mask 90 has small respiration exhaust holes 92 formed in a pattern of concentric rings in each side mask surface. Rather than a connector as shown in earlier mask embodiments, the oxygen mask 90 has a plug 94 attached to the tubular inlet 12. The plug 94 has a nipple to which is attached a separate tube 96 for introducing oxygen to the patient. A series of angular tapered accordion folds 98 are formed in the mask material above the nose portion, with each fold terminating at pivot point 97. When the folds 98 are expanded, as shown in FIG. 10, the mask 90 is of a size suitable for an adult male. Preferably, as shown in FIG. 10, the accordion folds 98 are integral with the material forming the top portion of the mask 90.

A snap or button 24 is associated with each accordion fold 98. The buttons 24 are mounted on pins 26 to separate slightly the buttons from the edges of the accordion folds 98. A band 28 is connected to the deformable metal strap 18 at its proximal end and defines one or more openings 30 at its distal end. The band 28 is formed from poly(vinyl chloride) resin or plastic material. Preferably, the band 28 has a thickness comparable to the distance of separation between the buttons 24 and the accordion folds 22. As shown in FIG. 10, the uppermost button is held within the most distant hole in the band 28. It would also be possible to leave the distal portion of the band 28 unattached to any button 24 associated with the accordion folds. In the preferred embodiment, the accordion folds 22 can be expanded to a fully open position such that the mask is suitable for use by a larger adult.

The size of the mask 90 is reduced to better fit the face of a smaller adult or a teenager or child by creasing or folding the mask material along the accordion folds 98. The folds are held in such creased or folded position by inserting one or more of the buttons 24 into holes or openings 30 in the band 28. Because the folds 98 have a tapered shape that terminates at point 97, they can be folded to reduce the mask size yet still permit the contours of the outer edges of the mask to better conform to the patient's face.

Each of the masks 10, 50, 80 and 90 may be modified also by incorporating a swivel joint connection as shown in FIG. 8. The inlet tube 62 has an inner diameter d1 at its proximal end and an annular groove 64 formed in its distal end. The inlet tube 62 usually is integral with the respiratory mask, and generally depends from a central portion of the mask that is proximate to a patient's nose when the mask is placed on a patient for respiratory treatment.

A connector 66 is snap fit into the inlet tube 62 during manufacture. The connector 66 has a tubular distal end and a ball joint 68 formed at its proximal end. The ball joint 68 defines an opening 72 such that the connector communicates with the inlet tube to permit gases or treating fluids to flow therethrough. The ball joint 68 is held within the annular groove 64 of the inlet tube 62. The ball joint 68 defines a center point 70 about which the ball joint may swivel. The center point 70 is positioned within the volume defined by the inlet tube between the uppermost edge of the annular groove and the lowermost edge of the annular groove. With this placement, the connector 66 swivels with respect to the inlet tube 62 so that the distal end of the connector can be moved away from a patient's face when a source tube for a gas treatment or a nebulizer is being connected. In addition, the swivel connection permits the patient to adjust the angle of the source tube for increased comfort.

A fifth preferred embodiment of a respiratory mask 110 is shown in FIGS. 11–13. In FIGS. 11–13, like parts are numbered with similar reference numerals to those used in FIGS. 1–5, preceded by a "1". The respiratory mask 110 includes a mask portion for covering the nose and mouth of a patient receiving a respiratory treatment. The mask 110 includes a tubular inlet 112 proximate to an upper or nose portion 113 of the mask 110. A connector (not shown) may be attached to the tubular inlet 112. A nebulizer (not shown) for delivering the respiratory treatment is in turn attached to the connector. The mask 110 further defines one or more exhaust ports 116, which are preferred when the mask 110 is used for aerosol or vapor treatments. Head strap brackets 134 are attached to the lateral edges on either side of the mask 110. One or more elastic head straps (not shown) may be threaded through the brackets 134 and wrapped around the patient's head to hold the mask 110 in place during treatment.

As in the embodiment shown in FIGS. 1–5, the mask 110 is provided with a deformable metal strap 118 attached by snaps 120. The metal strap 118 can be bent over the bridge of the patient's nose to help hold the mask 110 in place during treatment. The metal strap 118 can be made from, for example, aluminum.

The size of the mask 110 is adjustable by compression or expansion of accordion folds 122 arranged in a parallel array below the upper portion 113 of the mask 110. An adjustment member 150 is used to adjust the degree to which the accordion folds 122 are compressed. In this way the size of the mask 110 is adjusted along a vertical extent of the mask 110. When fully expanded, as shown in FIGS. 11 and 12, the mask 110 may be of a size suitable for an adult male. Compressing the accordion folds 122 adjusts the size of the mask 110 to fit smaller persons.

Each accordion fold 122 may comprise a rib or tube of stiffer material than the more resilient plastic material used to form the body of the mask 110. In this embodiment, each rib or tube is connected by a lateral edge to an adjacent rib or tube. Preferably, as shown in FIGS. 11 and 12, the accordion folds 122 are integral with the material forming the remainder of the mask 110.

The accordion folds 122 may also be made as a single continuous piece with and from the same injection-molded material as the remainder of the mask 110. The entire mask 110 may be formed from, for example, a single thickness of plastic material in order to simplify production. The accordion shape of the folds 122 allows for adjustment of mask size.

The adjustment member 150 is shown in detail in FIG. 13. Referring to FIGS. 11–13, the adjustment member 150 comprises a first bracket 152 and a second bracket 154 that is movable relative to the first bracket 152. The relative movement between the first and second brackets 152, 154 provides adjustment of the size of the mask 110 in the vertical direction.

The first bracket 152 includes a band portion 153 that is fixedly mounted below the nose portion 113, and is attached at each end to adjusting bars 158. The second bracket 154 includes a band portion 155 that is fixedly attached at a bottom portion 130 of the mask 110 below the accordion folds 122, and includes slots 160 for receiving the adjusting bars 158. Locking members 162 are pivotably mounted on the second bracket 154. The locking members 162 have proximal ends that selectively engage teeth 166 on the adjusting bars 158. The undersides of the teeth 166 slope upwardly so that the bottom portion 130 of the mask 110 can be easily pushed upwardly until a desired tooth 166 is engaged by the proximal end of a locking member, attaining the desired size of the mask 110. The distal ends of the locking members 162 can be pivoted inwardly (toward the mask as indicated by arrows in FIG. 13) in order to disengage the proximal ends of the locking members 162 from the teeth 166. The bottom mask portion 130 can then be lowered by extending the accordion members 122, thereby increasing the length of the mask 110. Alternatively, the bottom mask portion 130 can be raised, such as in the direction of arrow A in FIG. 12 to shorten the length of the mask 110.

Referring to FIG. 13, the band portion 155 of bracket 154 is shown in a first open position wherein the accordion folds would be extended or fully open. The band portion 155 is shown in phantom outline in a second more closed position wherein the accordion folds would be partly folded or compressed so that the mask would have a smaller size to fit a smaller sized patient. The locking members 162 are shown with proximal ends engaged to the teeth 166 when in the first open position, and are shown in phantom outline as pivoting inwardly to disengage the proximal ends from the teeth 166 when the band portion is moved upwardly to cause the accordion folds to be partly folded or compressed to reduce the mask size.

Preferably, the brackets 152, 154 are attached to the mask at one or more target protrusions or posts 170 extending outwardly from the mask 110. For example, three posts 170 can extend from the upper portion 113 of the mask 110 to mate with small cavities (not shown) in the band portion 153 and attach the bracket 152, and three posts 170 can be used to attach the band portion 155 of bracket 154 to bottom mask portion 130. The posts can be distributed across the width of the upper portion 113 and bottom portion 130 of the mask 110. The brackets 152, 154 slide over the posts in a manner similar to the attachment of an aluminum nose clip 118 to snaps 120. Alternatively, adhesive or glue may be used solely or in combination with protrusions or posts 170 to secure the brackets 152, 154 to the mask 110.

The first and second brackets 152, 154 can be made as, for example, integral molded plastic parts. Rigid but flexible plastics, such as ABS plastic or polypropylene are preferable.

The size of the mask 110 may also be adjusted using a button and snap arrangement as illustrated in FIGS. 1–5. A hook and loop fastener arrangement, as illustrated in FIGS. 6–9, or a band arrangement as shown in FIG. 10 may also be used. If any of these arrangements are used in the embodiment of FIGS. 10 and 11, the attachment points for the adjusting arrangement may be located at the bottom of the mask 110 and below the nose portion 113.

The mask 110 may be modified by incorporating a swivel joint connection as shown in FIG. 8.

The mask 110 illustrated in FIGS. 11–13 includes two exhaust ports 116, and has the form of an "aerosol" mask. Aerosol masks are used to deliver, for example, medicines to the patient in aerosol form from a nebulizer. The exhausts ports 116 allow the aerosol and gas in the mask 110 to escape.

In an alternative embodiment (not illustrated), the mask 110 has the form of a "partial rebreather" mask. In this embodiment, the exhaust ports 116 are replaced by a pattern of a plurality of small apertures on each side of the mask 110, similar to the exhaust holes 92 illustrated in FIG. 10. A reservoir bag, filled with oxygen, is connected to the tubular inlet 112. An exhalation port is located between the reservoir bag, as part of the bag assembly, and the mask 110.

In yet another alternative embodiment (not illustrated), the mask 110 has the form of a "nonrebreather" mask. In this embodiment, the exhaust ports 116 are replaced by a pattern of a plurality of apertures on each side of the mask 110, similar to the exhaust holes 92 illustrated in FIG. 10. The apertures can be arranged in a circular pattern, with a post in the center each pattern. Each post holds a one-way flap. When a patient inhales, the flaps close against the apertures, preventing outside air from entering the mask 110 through the apertures. The flap pushes away from the apertures when the patient exhales, allowing gases in the mask 110 to escape. An exhalation port is located between the reservoir bag and the mask 110.

In yet another alternative embodiment (not illustrated), the mask 110 has the form of a "venturi" mask. The venturi mask has exhaust ports or apertures, similar to the ports 116 shown in FIGS. 11–13, and is connected to a tube at the tubular inlet 112. A venturi is located in the tube, and adjustment of airflow through the venturi allows for very precise levels of oxygen to be provided to the patient.

In still yet another alternative embodiment (not illustrated), the mask 110 has the form of a "simple" mask. The simple mask has a plurality of small apertures on each side of the mask 110, similar to the exhaust holes 92 illustrated in FIG. 10. In this embodiment, the mask 110 is connected to an adapter at the tubular inlet 112, which is connected to oxygen tubing.

Preferably, the mask embodiments disclosed in this specification are fabricated from nonallergenic materials known to be suitable for contacting a patient's skin. Such materials include: thermoplastic resins, polyurethane resins, poly(vinyl chloride), polypropylene, polyethylene, polystyrene, SURLYN® from E.I. DuPont de Nemours & Company, Inc., or other plastics.

While specific embodiments of the invention have been described and illustrated, such embodiments should be considered illustrative of the invention only and not as limiting the invention as construed in accordance with the accompanying claims.

I claim:

1. A respiratory mask, comprising:
    an upper portion;
    a bottom portion;
    a plurality of accordion folds extending across a width of the mask between the upper portion and the bottom portion; and
    an adjustment member attached at the bottom portion of the mask,
    wherein the accordion folds are compressible along a length of the mask from an open position to a closed compressed position by adjustment of the adjustment member that maintains the folds in the closed compressed position to reduce a vertical size of the mask, wherein the adjustment member comprises a first bracket attached to the mask; and a second bracket movably engaged with the first bracket, wherein relative movement between the first and second brackets provides adjustment of the length of the mask.

2. The mask of claim 1, wherein the accordion folds are adjustable from an open position for a first mask size to a closed position for a second mask size.

3. The mask of claim 1, further comprising:
    a deformable strap bridging the upper portion of the mask, wherein the deformable strap is formed of bendable metal and is bendable to conform to the contours of a patient's nose to hold the mask in place.

4. The mask of claim 1, wherein the accordion folds are formed by one or more ribs connected by a flexible material.

5. The mask of claim 1, wherein the accordion folds are formed integrally with the upper and bottom portions of the mask.

6. The mask of claim 1, wherein:
    the first bracket comprises at least one adjustment arm having a plurality of teeth; and
    the second bracket comprises at least one locking member for engaging the teeth on the adjustment arm.

7. The mask of claim 1, wherein the mask is formed from a material selected from the group consisting of: thermoplastic resins, polyurethane resins, poly(vinyl chloride), polypropylene, polystyrene and polyethylene.

8. The mask of claim 1, further comprising:
    at least one exhaust port or a plurality of apertures disposed in the upper portion of the mask.

9. The mask of claim 5, further comprising:
    a tubular inlet disposed at the bottom of the upper portion of the mask.

10. The mask of claim 1, wherein the upper portion, the bottom portion and the accordion folds comprise a continuous piece of material.

11. The mask of claim 10, wherein the continuous piece of material forming the upper and bottom portions and the accordion folds is of substantially constant thickness.

12. A method of adjusting a respiratory mask, comprising:
    providing a mask comprising an upper portion, a bottom portion, and a plurality of accordion folds extending across a width of the mask between the upper portion and the bottom portion; and adjusting an adjustment member to open or close the folds and maintain the accordion folds in a desired unfolded or folded position so as to obtain a desired length along the vertical extent of the mask, wherein adjusting the adjustment member comprises:
    selectively engaging at least one locking member with a plurality of teeth.

13. The method of claim 12, wherein the accordion folds comprise one or more ribs connected by a flexible material.

14. The method of claim 12, wherein the upper portion, the bottom portion and the accordion folds comprise a continuous piece of material of substantially constant thickness.

15. A respiratory mask, comprising:
    an upper portion;
    a bottom portion;

an adjustable portion disposed between the upper portion and the bottom portion; and an adjustment member attached at the bottom portion of the mask, the adjustment member comprising at least one locking member and a plurality of teeth selectively engageable with the at least one locking member, wherein the adjustable portion is adjustable along a length of the mask by adjustment of the adjustment member.

16. The mask of claim 15, wherein the adjustment member further comprises:

a first bracket attached to the mask and including an adjustment arm onto which is disposed the plurality of teeth; and a second bracket movably engaged with the adjustment arm, the at least one locking member being disposed on the second bracket, wherein relative movement between the first and second brackets provides adjustment of the length of the mask.

17. The mask of claim 15, wherein the adjustable portion comprises:

a plurality of accordion folds.

18. The mask of claim 15, wherein the upper portion, the bottom portion and the adjustable portion comprise a continuous piece of material.

19. The mask of claim 18, wherein the continuous piece of material forming the upper and bottom portions and the adjustable portion is of substantially constant thickness.

* * * * *

UNITED STATES PATENT AND TRADEMARK OFFICE
CERTIFICATE OF CORRECTION

PATENT NO. : 7,121,279 B2 Page 1 of 1
APPLICATION NO. : 10/766413
DATED : October 17, 2006
INVENTOR(S) : Camell K. Dennis It is certified that error appears in the above-identified patent and that said Letters Patent is hereby corrected as shown below:

In Claim 9, at column 8, line 38, "9. The mask of claim 5, further comprising:" should read -- 9. The mask of claim 8, further comprising: --

Signed and Sealed this

Thirtieth Day of January, 2007

JON W. DUDAS
*Director of the United States Patent and Trademark Office*